(12) United States Patent
Iida et al.

(10) Patent No.: US 9,237,970 B2
(45) Date of Patent: Jan. 19, 2016

(54) MANUFACTURING METHOD AND APPARATUS FOR COMPOSITE BODY OF CONTINUOUS SHEET ASSOCIATED WITH ABSORBENT ARTICLE AND MANUFACTURING METHOD FOR ABSORBENT ARTICLE

(75) Inventors: Miwa Iida, Kagawa (JP); Osamu Ishikawa, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 232 days.

(21) Appl. No.: 13/819,723

(22) PCT Filed: Aug. 22, 2011

(86) PCT No.: PCT/JP2011/068842
§ 371 (c)(1),
(2), (4) Date: May 9, 2013

(87) PCT Pub. No.: WO2012/029572
PCT Pub. Date: Mar. 8, 2012

(65) Prior Publication Data
US 2013/0213570 A1    Aug. 22, 2013

(30) Foreign Application Priority Data

Aug. 30, 2010    (JP) ................................. 2010-192632

(51) Int. Cl.
*B29C 65/00* (2006.01)
*B32B 37/00* (2006.01)
(Continued)

(52) U.S. Cl.
CPC ..... *A61F 13/15577* (2013.01); *A61F 13/15699* (2013.01); *A61F 13/15723* (2013.01);
(Continued)

(58) Field of Classification Search
CPC ........ B32B 37/00; B32B 37/10; B29C 65/00; B29C 66/00145; B65H 5/00; B65H 5/02; B65H 5/04; B65H 5/08; B65H 5/22; B65H 7/00; B65H 20/00; B65H 20/12; B65H 29/00; B65H 29/003; B65H 29/06; B65H 29/16; B65H 29/24; B65H 29/241; B65H 29/242; B65H 29/243; B65H 29/245; B65H 29/38; B65H 29/40; B65H 29/68; B65H 35/00; B65H 35/0006; B65H 39/00
See application file for complete search history.

(56) References Cited

U.S. PATENT DOCUMENTS 3,093,528 A * 6/1963 Reich ............................ 156/285
4,556,443 A * 12/1985 Moya ............................ 156/356
(Continued)

FOREIGN PATENT DOCUMENTS

JP    64-008184      1/1989
JP    2002-516802 A  6/2002
(Continued)

OTHER PUBLICATIONS

Chinese Office Action from corresponding Chinese application No. 201180041753.1 dated May 5, 2014 (8 pgs).
(Continued)

*Primary Examiner* — Michael N Orlando
*Assistant Examiner* — Matthew Hoover
(74) *Attorney, Agent, or Firm* — Brinks Gilson & Lione (57) ABSTRACT

There is provided a manufacturing method for a composite body of a continuous sheet associated with an absorbent article, the composite body being manufactured by attaching a single-cut sheet to the continuous sheet at a predetermined attachment pitch. The method includes: holding the single-cut sheet by a holding section in surface-to-surface contact, the holding section moving along a path; weakening a holding force by which the single-cut sheet is held; exerting a suction force on the single-cut sheet through the continuous sheet, the suction force causing the single-cut sheet to be sucked toward the continuous sheet; and when the holding section passes a delivery position set on the path, separating the single-cut sheet from the holding section, and delivering the single-cut sheet to the continuous sheet by attaching the single-cut sheet to the continuous sheet without pinching the single-cut sheet between the holding section and the continuous sheet due to the weakening and the exerting, the continuous sheet being running through a neighboring position near the delivery position.

6 Claims, 6 Drawing Sheets

(51) Int. Cl.
- B65H 5/00 (2006.01)
- B65H 5/02 (2006.01)
- B65H 5/06 (2006.01)
- B65H 5/08 (2006.01)
- B65H 5/22 (2006.01)
- B65H 7/00 (2006.01)
- B65H 7/16 (2006.01)
- B65H 29/00 (2006.01)
- B65H 29/24 (2006.01)
- A61F 13/15 (2006.01)
- B32B 37/10 (2006.01)
- B65H 39/00 (2006.01)
- B65H 35/00 (2006.01)
- B65H 20/12 (2006.01)
- B65H 29/68 (2006.01)
- B65H 29/16 (2006.01)
- B65H 29/06 (2006.01)
- B65H 29/40 (2006.01)
- B65H 29/38 (2006.01)
- B65H 20/00 (2006.01)
- B65H 5/04 (2006.01)

(52) U.S. Cl.
CPC ..... *A61F13/15756* (2013.01); *A61F 13/15764* (2013.01); *B29C 65/00* (2013.01); *B29C 66/00145* (2013.01); *B32B 37/00* (2013.01); *B32B 37/10* (2013.01); *B65H 5/00* (2013.01); *B65H 29/00* (2013.01); *B65H 35/00* (2013.01); *B65H 39/00* (2013.01); *B65H 5/02* (2013.01); *B65H 5/04* (2013.01); *B65H 5/08* (2013.01); *B65H 5/22* (2013.01); *B65H 7/00* (2013.01); *B65H 20/00* (2013.01); *B65H 20/12* (2013.01); *B65H 29/003* (2013.01); *B65H 29/06* (2013.01); *B65H 29/16* (2013.01); *B65H 29/24* (2013.01); *B65H 29/241* (2013.01); *B65H 29/242* (2013.01); *B65H 29/243* (2013.01); *B65H 29/245* (2013.01); *B65H 29/38* (2013.01); *B65H 29/40* (2013.01); *B65H 29/68* (2013.01); *B65H 35/0006* (2013.01); *B65H 35/006* (2013.01); *Y10T 156/17* (2015.01)

(56) References Cited

U.S. PATENT DOCUMENTS

| | | | | |
|---|---|---|---|---|
| 4,726,876 | A | * | 2/1988 | Tomsovic, Jr. .............. 156/552 |
| 5,224,405 | A | * | 7/1993 | Pohjola .............. 83/24 |
| 6,165,306 | A | | 12/2000 | Rajala |
| 6,645,330 | B2 | * | 11/2003 | Pargass et al. .............. 156/73.1 |
| 6,915,829 | B2 | * | 7/2005 | Popp et al. .............. 156/519 |
| 2004/0089403 | A1 | * | 5/2004 | Satoh .............. 156/160 |
| 2009/0320663 | A1 | | 12/2009 | Yamamoto |

FOREIGN PATENT DOCUMENTS

| | | |
|---|---|---|
| JP | 2002-193440 A | 7/2002 |
| JP | 2004-148040 A | 5/2004 |
| JP | 2006-55382 A | 3/2006 |
| JP | 2010-142415 A | 7/2010 |
| WO | WO 99/62801 | 12/1999 |
| WO | WO 2010/071069 | 6/2010 |

OTHER PUBLICATIONS

European extended Search Report from corresponding European application No. 11821589.6 dated Jun. 5, 2014 (4 pgs).
International Search Report from corresponding PCT application No. PCT/JP2011/068842 dated Nov. 15, 2011 (4 pgs).

* cited by examiner

B-B CROSS SECTION

MANUFACTURING METHOD AND APPARATUS FOR COMPOSITE BODY OF CONTINUOUS SHEET ASSOCIATED WITH ABSORBENT ARTICLE AND MANUFACTURING METHOD FOR ABSORBENT ARTICLE

RELATED APPLICATION

The present application is a 35 U.S.C. §371 national stage filing of International Patent Application No. PCT/JP2011/068842, filed Aug. 22, 2011, to which priority is claimed under 35 U.S.C. §120 and through which priority is claimed under 35 U.S.C. §119 to Japanese Priority Patent Application No. 2010-192632, filed Aug. 30, 2010.

TECHNICAL FIELD

The present invention relates to a manufacturing method and an apparatus for a composite body of a continuous sheet associated with an absorbent article such as disposable diapers, and a manufacturing method for such an absorbent article.

BACKGROUND ART

Figure 1:
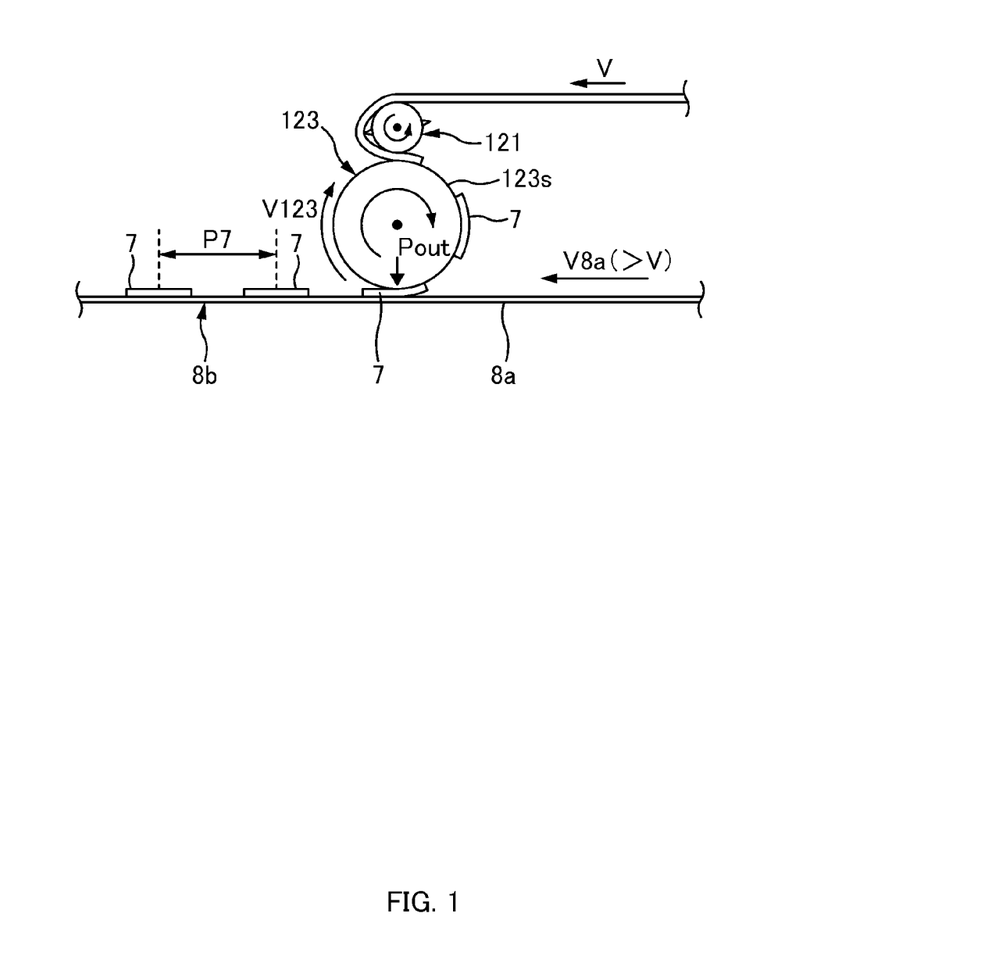
FIG. 1 is a view illustrating a conventional manufacturing method.

In a conventional production line for an absorbent article such as disposable diapers and sanitary napkins, as shown in a schematic side view of FIG. 1, single-cut sheets 7 made of a soft nonwoven fabric or the like are attached to a continuous sheet 8a made of a soft nonwoven fabric or the like at a predetermined attachment pitch P7 in the direction in which the continuous sheet 8a extends.

As an example of the above method, PLT 1 describes a method as follows. First, the single-cut sheets 7 cut off by a cutter roller 121 are sucked to and held on an outer circumferential surface 123s of a rotating anvil roller 123 at a predetermined pitch in the circumferential direction. Also, at a predetermined position Pout (hereinafter referred to as a "delivery position Pout") of the outer circumferential surface 123s in the circumferential direction, the continuous sheet 8a is fed so as to run along the tangent of the outer circumferential surface 123s. An adhesive (not shown) is previously applied to portions of the continuous sheet 8a on which the single-cut sheets 7 are to be placed. Thus, when each single-cut sheet 7 held on the outer circumferential surface 123s passes the delivery position Pout, a portion thereof that is passing the delivery position Pout is sequentially attached and delivered to the continuous sheet 8a.

CITATION LIST

Patent Literature

[PLT 1] JP 2006-55382A

SUMMARY OF INVENTION

Technical Problem

However, in the above method, if the single-cut sheets 7 held on the outer circumferential surface 123s are attached to the continuous sheet 8a while being pressed against the surface thereof, there is a possibility that the single-cut sheets 7 or the like becomes wrinkled during the attaching if there is a difference in speed (relative speed) between a peripheral speed V123 of the anvil roller 123 and a running speed V8a of the continuous sheet 8a.

The above problem will be described in detail. First, in the above method, the single-cut sheets 7, which are held on the outer circumferential surface 123s of the anvil roller 123, are rotating at the same speed as the peripheral speed V123 of the anvil roller 123. In the above method, also, the single-cut sheets 7 passing the delivery position Pout, which are being pressed against the continuous sheet 8a by the outer circumferential surface 123s of the anvil roller 123, are in a state of being physically sandwiched between the outer circumferential surface 123s of the anvil roller 123 and the continuous sheet 8a. In this sandwiched state, the sheet 7 (8a) moving at higher speed is restrained by the sheet 8a (7) moving at lower speed. This causes the sheet 7 (8a) moving at higher speed to buckle, which results in wrinkling.

For example, if the running speed V8a of the continuous sheet 8a is lower than the peripheral speed V123 of the anvil roller 123, the single-cut sheets 7 will become wrinkled. Since such wrinkles worsen the appearance and the touch, the commodity value of the absorbent article may be degraded.

Therefore, in use of the above method, it is necessary to synchronize the peripheral speed V123 of the anvil roller 123 and the running speed V8a of the continuous sheet 8a with each other so that these speeds are equal to each other.

However, no matter how precisely synchronized, the two speeds cannot be made completely equal to each other: i.e., in reality, they have a certain amount of speed difference from each other. As a result, in the above method, the occurrence of wrinkles cannot be avoided, and thus there is no other choice but to accept the occurrence of wrinkles to some extent.

In view of the conventional problem described above, an object of the present invention is to prevent the occurrence of wrinkles at the time of attaching a single-cut sheet to a continuous sheet.

Solution to Problem

In order to address the above-described problem, a primary aspect of the invention is a manufacturing method for a composite body of a continuous sheet associated with an absorbent article, the composite body being manufactured by attaching a single-cut sheet to the continuous sheet at a predetermined attachment pitch, the method including:

holding the single-cut sheet by a holding section in surface-to-surface contact, the holding section moving along a path;

weakening a holding force by which the single-cut sheet is held;

exerting a suction force on the single-cut sheet through the continuous sheet, the suction force causing the single-cut sheet to be sucked toward the continuous sheet; and when the holding section passes a delivery position set on the path, separating the single-cut sheet from the holding section, and delivering the single-cut sheet to the continuous sheet by attaching the single-cut sheet to the continuous sheet without pinching the single-cut sheet between the holding section and the continuous sheet due to the weakening and the exerting, the continuous sheet being running through a neighboring position near the delivery position.

Further, a manufacturing apparatus for a composite body of a continuous sheet associated with an absorbent article, the composite body being manufactured by attaching a single-cut sheet to the continuous sheet at a predetermined attachment pitch, the apparatus including:
- a holding section that moves along a path while holding the single-cut sheet in a surface-to-surface contact;
- a running mechanism by which the continuous sheet runs through a neighboring position near a delivery position that is set on the path;
- a holding-force adjustment mechanism that weakens a holding force of the holding section in order to separate the single-cut sheet from the holding section when the holding section passes the delivery position, the holding section holding the single-cut sheet by the holding force; and
- a sucking mechanism
  - that is disposed at at least the neighboring position and that attaches the single-cut sheet to the continuous sheet without pinching the single-cut sheet between the holding section and the continuous sheet due to exerting a suction force on the single-cut sheet through the continuous sheet, the suction force causing the single-cut sheet to be sucked toward the continuous sheet.

Features of the invention other than the above will become clear by reading the description of the present specification with reference to the accompanying drawings.

Advantageous Effects of Invention

According to the present invention, the occurrence of wrinkles at the time of adhering a single-cut sheet to a continuous sheet can be prevented or reduced.

DESCRIPTION OF EMBODIMENTS

At least the following matters will be made clear by the explanation in the present specification and the description of the accompanying drawings.

A manufacturing method for a composite body of a continuous sheet associated with an absorbent article, the composite body being manufactured by attaching a single-cut sheet to the continuous sheet at a predetermined attachment pitch, the method including:
- holding the single-cut sheet by a holding section in surface-to-surface contact, the holding section moving along a path;
- weakening a holding force by which the single-cut sheet is held;
- exerting a suction force on the single-cut sheet through the continuous sheet, the suction force causing the single-cut sheet to be sucked toward the continuous sheet; and
- when the holding section passes a delivery position set on the path,
  - separating the single-cut sheet from the holding section, and
  - delivering the single-cut sheet to the continuous sheet by attaching the single-cut sheet to the continuous sheet without pinching the single-cut sheet between the holding section and the continuous sheet due to the weakening and the exerting, the continuous sheet being running through a neighboring position near the delivery position.

According to the manufacturing method for a composite body of a continuous sheet associated with an absorbent article described above, the single-cut sheet is attached to the continuous sheet without being pinched between the holding section and the continuous sheet when passing the delivery position. Therefore, the single-cut sheet is free from being substantially captured by the holding section at the moment of being attached to the continuous sheet. In other words, the single-cut sheet is in a state of easily conforming to the continuous sheet to which it is to be attached to; for example, the single-cut sheet is likely to change its state according to the circumstances at the time of attaching to the continuous sheet. Accordingly, wrinkling of the single-cut sheet and the continuous sheet caused by a speed difference between the turning speed of the holding section and the running speed of the continuous sheet is effectively prevented.

In such a manufacturing method for a composite body of a continuous sheet associated with an absorbent article, it is desirable that
- a pair of press rollers that rotate with their outer circumferential surfaces facing each other are disposed at a position downstream from the neighboring position on a running path of the continuous sheet, and
- when passing a nip between the press rollers, the continuous sheet and the single-cut sheet that is placed on the continuous sheet are pressed by the outer circumferential surfaces of the press rollers in a direction which the single-cut sheet is placed on the continuous sheet.

According to the manufacturing method for a composite body of a continuous sheet associated with an absorbent article described above, the continuous sheet and the single-cut sheet placed thereon are pressed by the press rollers after the single-cut sheet is attached to the continuous sheet. Therefore, the single-cut sheet can be attached to the continuous sheet firmly.

In such a manufacturing method for a composite body of a continuous sheet associated with an absorbent article, it is desirable that
- a size of a spacing between the holding section and the continuous sheet at the delivery position is set to a value more than 1.0 times and less than 3.0 times as large as the maximum thickness of the single-cut sheet.

According to the manufacturing method for a composite body of a continuous sheet associated with an absorbent article described above, the size of the spacing can be certainly made larger than the thickness of the single-cut sheet. Therefore, it is ensured that the single-cut sheet can be adhered to the continuous sheet in the delivery position without being pinched between the holding section and the continuous sheet.

In such a manufacturing method for a composite body of a continuous sheet associated with an absorbent article, it is desirable that
- a suction mechanism is provided at the neighboring position, the suction mechanism sucking air through the continuous sheet in a direction in which the single-cut sheet is separated from the holding section passing the delivery position, and an air permeability of the continuous sheet is higher than that of the single-cut sheet.

According to the manufacturing method for a composite body of a continuous sheet associated with an absorbent article described above, the suction of the suction mechanism can be effectively exerted on the single-cut sheet through the continuous sheet, whereby the single-cut sheet can be swiftly sucked toward the continuous sheet. Thus, the single-cut sheet can be transferred to the continuous sheet smoothly.

In such a manufacturing method for a composite body of a continuous sheet associated with an absorbent article, it is desirable that a suction mechanism is provided at the neighboring position, the suction mechanism sucking air through the continuous sheet in a direction in which the single-cut sheet is separated from the holding section passing the delivery position, and a suction amount of the suction mechanism is increased/decreased according to an increase/decrease of a running speed of the continuous sheet.

According to the manufacturing method for a composite body of a continuous sheet associated with an absorbent article described above, it is possible to prevent variations in the attachment pitch of the single-cut sheets that may occur when the running speed of the continuous sheet.

A manufacturing method for an absorbent article using a composite body that is manufactured in such a method, wherein
   the absorbent article includes
      an absorbent main body that has an absorbent body for absorbing a liquid and is brought into contact with a crotch of a wearer,
      a pair of side sheets attached to both end portions of the absorbent main body in the width direction, and
      a side flap attached to each of the side sheets so as to protrude outwardly in the width direction from an edge of the absorbent main body in the width direction,
   the continuous sheet is a base material of the side sheet that has not been divided into a piece of the side sheet,
   the single-cut sheet is the side flap,
   the absorbent main body has a top sheet covering the absorbent body, and
   the composite body is attached to a continuous sheet of the top sheet after manufacturing the composite body.

According to the manufacturing method for an absorbent article described above, it is possible to manufacture a preferable absorbent article in which wrinkling of the side flaps caused when the side flaps are attached to the side sheets is reduced.

Further,

A manufacturing apparatus for a composite body of a continuous sheet associated with an absorbent article, the composite body being manufactured by attaching a single-cut sheet to the continuous sheet at a predetermined attachment pitch, the apparatus including:
   a holding section that moves along a path while holding the single-cut sheet in a surface-to-surface contact;
   a running mechanism by which the continuous sheet runs through a neighboring position near a delivery position that is set on the path;
   a holding-force adjustment mechanism that weakens a holding force of the holding section in order to separate the single-cut sheet from the holding section when the holding section passes the delivery position, the holding section holding the single-cut sheet by the holding force; and
   a sucking mechanism
      that is disposed at at least the neighboring position and that attaches the single-cut sheet to the continuous sheet without pinching the single-cut sheet between the holding section and the continuous sheet due to exerting a suction force on the single-cut sheet through the continuous sheet, the suction force causing the single-cut sheet to be sucked toward the continuous sheet.

According to the manufacturing apparatus for a composite body of a continuous sheet associated with an absorbent article described above, the single-cut sheet is adhered to the continuous sheet without being pinched between the holding section and the continuous sheet when passing through the delivery position. Therefore, the single-cut sheet is free from being captured by the holding section at the time of being adhered to the continuous sheet, leaving the single-cut sheet in a state of easily conforming to the continuous sheet to which it is to be adhered to, such as easily changing its state according to the circumstances at the time of adhering to the continuous sheet. Accordingly, wrinkling of the single-cut sheet and the continuous sheet caused by a speed difference between the turning speed of the holding section and the running speed of the continuous sheet is effectively prevented or reduced.

—First Embodiment—

Figure 2:
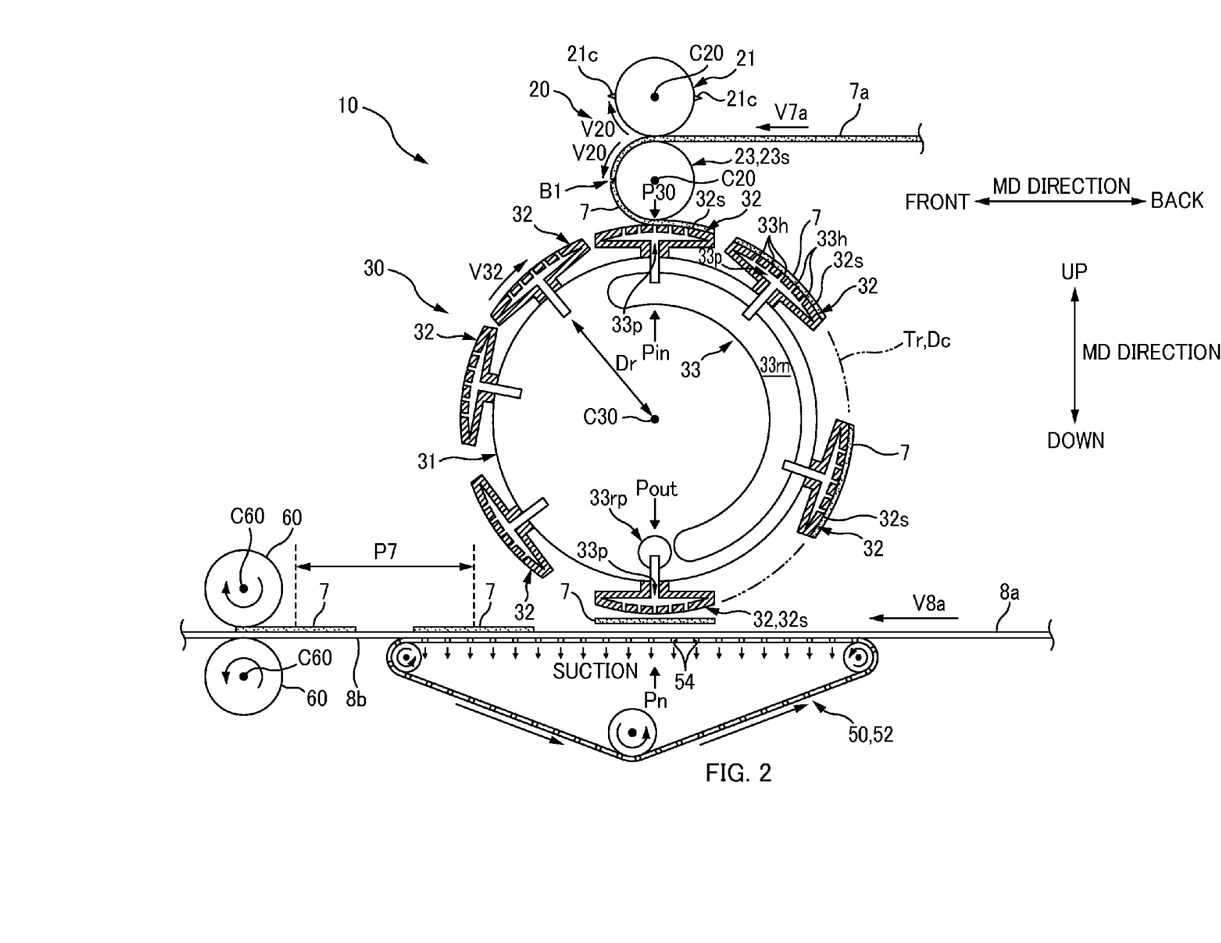
FIG. 2 is a schematic side view of a manufacturing apparatus 10 for a composite body 8b of a continuous sheet 8a in the first embodiment.

FIG. 2 is a schematic side view of a manufacturing apparatus 10 for a composite body 8b of a continuous sheet 8a in the first embodiment, where the configuration of part of the apparatus, such as holding pads 32 and an endless belt 52, is shown in vertical section. Note that, as used herein, the width direction of a second continuous sheet 8a as the "continuous sheet" in the claims is referred to as a CD direction. The CD direction is orthogonal to a running direction in which the second continuous sheet 8a extends, and is the direction perpendicular to the paper surface in FIG. 2. Note also that a direction orthogonal to the CD direction is referred to as an MD direction. In other words, the MD direction is any direction parallel to the paper surface in FIG. 2, and more specifically, any direction defined by the up-down direction and the front-back direction orthogonal to each other as shown in FIG. 2.

The manufacturing apparatus 10 includes: (1) a cutter apparatus 20 that produces a single-cut sheet 7 having a predetermined length by cutting off a leading portion of a first continuous sheet 7a which is made of a nonwoven fabric or the like and is being fed continuously in the MD direction; and (2) an attaching apparatus 30 that produces a composite body 8b of the continuous sheet 8a by receiving the single-cut sheet 7 from the cutter apparatus 20 and attaching at a predetermined attachment pitch P7 the single-cut sheet 7 to the second continuous sheet 8a which is made of a nonwoven fabric or the like and is running continuously in the MD direction.

In this example, a nonwoven fabric or a composite material of a nonwoven fabric and an elastic material (film, thread, etc.) is used as the first continuous sheet 7a, which has a basis weight of 20 to 110 ($g/m^2$) and a thickness of 0.2 to 3.0 (mm). The second continuous sheet 8a is also made of a nonwoven fabric, and has a basis weight of 15 to 50 ($g/m^2$) and a thickness of 0.1 to 2.0 (mm).

The cutter apparatus 20 has, for example, a pair of upper and lower rollers 21 and 23 of which rotary axes C20 extend in the CD direction. The upper roller 21 is a cutter roller 21 having cutter blades 21c which protrude from the outer circumferential surface thereof. The lower roller 23 is an anvil roller 23 having a flat outer circumferential surface 23s which is for receiving the cutter blades 21c. These rollers 21 and 23 are driven to rotate in the opposite directions to each other at a predetermined peripheral speed V20, and the first continuous sheet 7a that is the base material of the single-cut sheets 7 is fed to the nip between the rollers 21 and 23. The first continuous sheet 7a is sucked to and held on the outer circumferential surface 23s of the anvil roller 23 by suction from the outer circumferential surface 23s, where the first continuous sheet 7a is transported in an integrated manner with the outer circumferential surface 23s. During this transportation, when each cutter blade 21c comes to face the outer circumferential surface 23s of the anvil roller 23 by the rotation of the cutter roller 21, a leading portion of the first continuous sheet 7a is cut off to produce the single-cut sheet 7. The produced single-cut sheet 7 is transported down to a position P30 facing the attaching apparatus 30 while being held on the outer circumferential surface 23 by the suction of the anvil roller 23. Then, the single-cut sheet 7 is delivered to the attaching apparatus 30 at the position P30.

Incidentally, the peripheral speed V20 (m/sec) of the anvil roller 23 and the feeding speed V7a (m/sec) of the first continuous sheet 7a are set to be approximately equal to each other, whereby the first continuous sheet 7a is held on the outer circumferential surface 23s of the anvil roller 23 substantially without causing relative sliding. As a result, substantially no gap is generated at a division position B1 between the single-cut sheets 7 adjacent in the running direction on the outer circumferential surface 23s.

The attaching apparatus 30 has a plurality of holding pads 32 (corresponding to the holding sections) that hold the single-cut sheets 7. The holding pads 32 move along a predetermined path Tr in one direction (clockwise in FIG. 2) while maintaining their arrangement in a row. The path Tr is set so as to have a shape of a precise circle whose center is a turning axis C30 extending in the CD direction.

Each of the holding pads 32 has a roughly-arc-shaped surface 32s extending along the path Tr and facing outward in a turning-radius direction Dr. The roughly-arc-shaped surface 32s serves as the holding surface 32s, and thereby each holding pad 32 holds in surface-to-surface contact one single-cut sheet 7 sent from the cutter apparatus 20. Specifically, a receipt position Pin where the single-cut sheet 7 is received is set at the top end position of the path Tr that faces the outer circumferential surface 23s of the anvil roller 23. When passing through the receipt position Pin, the holding pad 32 receives in surface-to-surface contact the single-cut sheet 7 on its holding surface 32s from the anvil roller 23.

Also, at the bottom end position of the path Tr, a delivery position Pout is set at which the single-cut sheet 7 held by the holding pad 32 is delivered to the second continuous sheet 8a. That is, the running path of the second continuous sheet 8a is set as a path that passes a neighboring position Pn near the delivery position Pout and that is in parallel with the tangent of the path Tr at the delivery position Pout. Therefore, when the holding pad 32 passes the delivery position Pout, the single-cut sheet 7 on the holding pad 32 is attached to and delivered to the second continuous sheet 8a with the assistance of the action of an adhesive (not shown) applied in advance to the second continuous sheet 8a.

Note that the holding force for holding the single-cut sheet 7 on the holding surface 32s of the holding pad 32 is imparted by a holding-force imparting mechanism 33, which will be described later. Note also that the running path of the second continuous sheet 8a is formed by a suction belt conveyer 50, which will also be described later.

As shown in FIG. 2, the alignment pitch of the holding pads 32 in a circling direction Dc is predetermined in correspondence with the positions thereof in the circling direction Dc. For example, the holding pads 32 are configured to move with a substantially narrow gap between the holding pads 32 adjacent in the circling direction Dc at the receipt position Pin, but move with a largely widened gap therebetween at the delivery position Pout.

With the above configuration, at the receipt position Pin, each holding pad 32 can receive a to-be-received single-cut sheet 7 with substantially no gap formed between that single-cut sheet 7 and its adjacent single-cut sheet 7. Also, at the delivery position Pout, each holding pad 32 can deliver that single-cut sheet 7 to the second continuous sheet 8a in a discontinuous arrangement having a large gap between that single-cut sheet 7 and its adjacent single-cut sheet 7. Note that the gap between the adjacent holding pads 32 at the delivery position Pout is set in size so as to correspond to the attachment pitch P7 at which the single-cut sheets 7 are to be attached to the second continuous sheet 8a.

The turning speed V32 (m/sec) of the holding pads 32 at the receipt position Pin is set so as to be approximately the same as the peripheral speed V20 of the anvil roller 23 of the cutter apparatus 20. In other words, the turning speed V32 of the holding pads 32 at the position Pin is controlled to fall within ±10% of the peripheral speed V20 of the anvil roller 23. By this setting, the single-cut sheet 7 is held on the holding surface 32s of the holding pad 32 in a state of having substantially no wrinkles.

Similarly, the turning speed V32 of the holding pads 32 at the delivery position Pout is set so as to be approximately the same as the running speed V8a (m/sec) of the second continuous sheet 8a. In other words, the turning speed V32 of the holding pads 32 at the position Pout is controlled to fall within ±5% of the running speed V8a of the second continuous sheet 8a. This prevents wrinkles from occurring at the delivery position Pout on the single-cut sheets 7 or the like. Note that the running speed V8a of the second continuous sheet 8a is set so as to be higher than the peripheral speed V20 of the anvil roller 23. Thereby, the single-cut sheets 7 are attached to the second continuous sheet 8a at the attachment pitch P7, which is the discontinuous arrangement as described above.

The foregoing movement of the holding pads 32 while changing their alignment pitch and turning speed V32 according to their respective positions in the circling direction Dc is realized by a well-known mechanism. For example, such a mechanism has: a rotary drum 31 that is driven and rotates about the turning axis C30 extending in the CD direction; and a drive mechanism (not shown) such as a cam mechanism that reciprocates the holding pads 32 with respect to the rotary drum 31 over a predetermined range in the circumferential direction of the rotary drum 31. Combination of the above reciprocating operation and the rotating operation of the rotary drum 31 enables the holding pads 32 to move while changing their alignment pitch and turning speed V32.

Incidentally, in the first embodiment, the configuration is designed in order to prevent wrinkles that may occur at the time of attaching the single-cut sheets 7 to the second continuous sheet 8a. This technique will be described hereinafter.

First, the basic idea for wrinkle prevention will be described. Basically, wrinkles are likely to occur when there is a difference between the turning speed V32 of the holding pads 32 and the running speed V8a of the second continuous sheet 8a at the delivery position Pout and the single-cut sheet 7 is in a pinched state between the holding pad 32 and the second continuous sheet 8a at the delivery position Pout.

The speed difference as the first cause can be reduced by synchronizing the two speeds with each other. Therefore, in this example, the turning speed V32 of the holding pads 32 is set so as to fall within ±5% of the running speed V8a of the second continuous sheet 8a as described above. However, it is impossible to eliminate this speed difference completely. In other words, the turning speed V32 of the holding pads 32 and the running speed V8a of the second continuous sheet 8a cannot be made completely equal to each other.

In view of the above, in the first embodiment, the prevention of the wrinkles is achieved by eliminating the pinched state at the delivery position Pout as the second cause.

Figure 3:
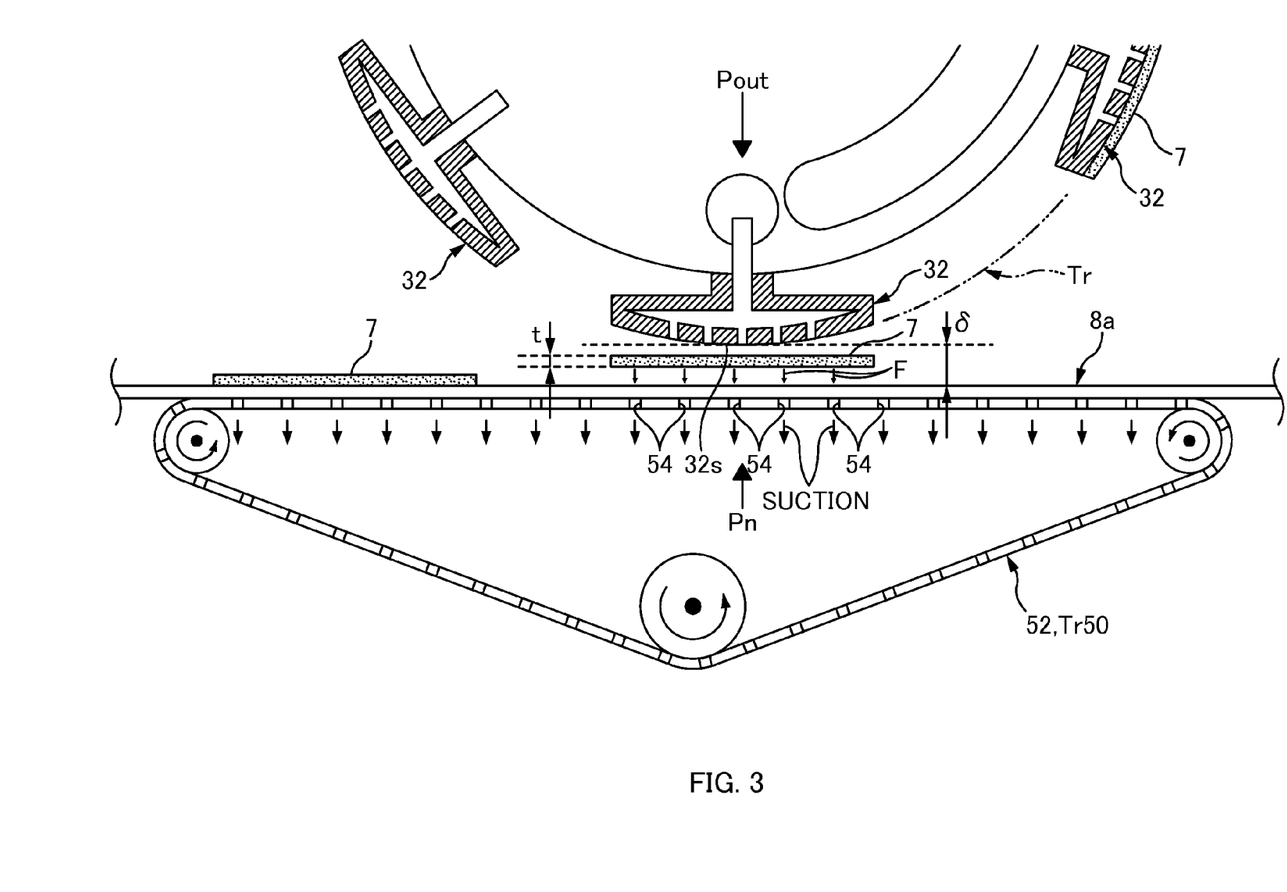
FIG. 3 is an enlarged side view of a delivery position Pout in the manufacturing apparatus 10.

More specifically, the prevention of the wrinkles is achieved as follows: as shown in the magnified view of the delivery position Pout in FIG. 3, the spacing δ at the delivery position Pout between the holding surface 32s of the holding pad 32 and the second continuous sheet 8a is set so as to be more than 1.0 times and less than 3.0 times as large as the maximum thickness t of the single-cut sheet 7 (more preferably, more than 1.0 times and less than 2.0 times as large as the maximum thickness t of the single-cut sheet 7); and the single-cut sheet 7 on the holding surface 32s is sucked at the delivery position Pout toward the second continuous sheet 8a.

With the above configuration, when passing the delivery position Pout, the single-cut sheet 7 substantially jumps from the holding surface 32s to the second continuous sheet 8a without being pinched between the holding surface 32s and the second continuous sheet 8a. As a result, the single-cut sheet 7 and the second continuous sheet 8a are attached together while being effectively prevented from wrinkling.

More specifically, at the instant of attaching the single-cut sheet 7 to the second continuous sheet 8a, the single-cut sheet 7 is substantially out of contact with the holding pad 32, and thus, with no more being captured by the holding pad 32. Therefore, the single-cut sheet 7 is in a state of easily conforming to the second continuous sheet 8a; for example, the single-cut sheet 7 is likely to change its state freely according to attachment conditions to the second continuous sheet 8a. Accordingly, even if there is a speed difference between the turning speed V32 of the holding pad 32 and the running speed V8a of the second continuous sheet 8a, wrinkling of the single-cut sheet 7 and the second continuous sheet 8a caused by the speed difference is effectively prevented.

Note that the "maximum thickness t" described above refers to the maximum value of the thickness of the single-cut sheet 7 in its natural state free from being subject to any external force. Concerning a measurement of the spacing 5 between the holding surface 32s of the holding pad 32 and the second continuous sheet 8a at the delivery position Pout, it is desirable to perform the measurement while the suction belt conveyer 50 (to be described later) is sucking the second continuous sheet 8a onto an endless belt of the conveyer 50. However, in some cases, the measurement may be performed without the foregoing suction.

As the mechanism for the above substantial jumping (corresponding to the sucking mechanism and the suction mechanism), the suction belt conveyer 50 that forms the running path of the second continuous sheet 8a is used in this example, and the suction belt conveyer 50 is disposed extending in the MD direction over the neighboring position Pn near the delivery position Pout.

More specifically, the suction belt conveyer 50 (corresponding to the running mechanism) has an endless belt 52 that runs along a roughly triangular path Tr50. Throughout the substantially-entire placement surface of the endless belt 52, a plurality of suction holes 54 are distributed in a substantially uniform manner in such a pattern as a zigzag pattern or a lattice pattern. By the suction through the suction holes 54, the second continuous sheet 8a is sucked onto the placement surface in an integrated manner.

One side of the roughly triangular path Tr50 extends in a direction parallel to the tangent of the path Tr of the holding pads 32 at the delivery position Pout, and the suction through the suction holes 54 is continuously performed through the almost entire length of the one side. Therefore, the second continuous sheet 8a runs on a straight path along a direction parallel to the tangent of the path Tr at the delivery position Pout and in an integrated manner with the endless belt 52.

Also, since the suction through the suction holes 54 is performed over the entire length of the one side as described above, it also acts onto the single-cut sheet 7 on the holding pad 32 through the second continuous sheet 8a when the holding pad 32 passes the delivery position Pout. By a suction force F of this suction, the entirety of the single-cut sheet 7 is sucked toward the second continuous sheet 8a substantially at the same time, and substantially jumps thereto. Then, the single-cut sheet 7 is bonded to the second continuous sheet 8a.

Note that, since the suction force F at the time of the substantial jumping of the single-cut sheet 7 is caused by the suction of the suction belt conveyer 50 acting on the single-cut sheet 7 through the second continuous sheet 8a, it is necessary that the second continuous sheet 8a has some degree of air permeability in its thickness direction. Moreover, it is desirable that the air permeability of the second continuous sheet 8a be higher than that of the single-cut sheet 7. Having such a second continuous sheet, the suction of the suction belt conveyer 50 can effectively act on the single-cut sheet 7 through the second continuous sheet 8a, which permits the single-cut sheet 7 to jump to the second continuous sheet 8a more swiftly. Incidentally, the air permeability, which is generally also referred to as the ventilation rate ($cc/(cm^2 \times sec)$), is measured by JIS L1096 Air Permeability A Method (Frazier method), etc., for example.

In addition, in order to ensure the above jumping, in this example, the holding force imparted to the holding surface 32s of the holding pad 32 is weakened in the delivery position Pout. More specifically, as shown in FIG. 2, in order to hold the single-cut sheet 7, the holding force is imparted to the holding surface 32s of the holding pad 32 in the range of the path Tr from the receipt position Pin to immediately before the delivery position Pout. When the holding pad 32 arrives at the delivery position Pout, the holding force is released (that is, becomes zero) through the almost entirety of the holding surface 32s. Therefore, the single-cut sheet 7 is separated and jumps smoothly from the holding surface 32s.

The above imparting and releasing of the holding force are performed by a holding-force imparting mechanism 33 (corresponding to the holding-force adjustment mechanism). The holding-force imparting mechanism 33 includes: a plurality of suction holes 33h formed on the holding surface 32s of each holding pad 32; an air flow path 33p that is formed inside the holding pad 32 and communicates with the suction holes 33h; and a negative pressure chamber 33rn (a chamber 33rn having a lower barometric pressure than around the holding surface 32s) placed so that when a holding pad 32 is located within a predetermined range of the path Tr, the air flow path 33p of that holding pad 32 communicates with the chamber 33rn.

The above predetermined range for the negative pressure chamber 33rn is set to a range from the receipt position Pinto immediately before the delivery position Pout. Thus, the delivery position Pout is out of the predetermined range. Therefore, when the holding pad 32 passes the delivery position Pout, the suction through all the suction holes 33h on the holding surface 32s is stopped substantially at the same time, which causes the holding force to become zero through the almost entirety of the holding surface 32s. The holding force keeps being zero approximately until immediately before the holding pad 32 arrives at the receipt position Pin again. That is, once the holding pad 32 arrives at the receipt position Pin, the air flow path 33p of the holding pad 32 communicates with the negative pressure chamber 33rn. Thus, all the suction holes 33h on the holding surface 32s of the holding pad 32 restart the once-suspended suction substantially at the same time.

Here, as shown in FIG. 2, it is desirable to configure the holding pad 32 so that, once the holding pad 32 arrives at the delivery position Pout, the air flow path 33p thereof communicates with a positive pressure chamber 33rp (a chamber 33rp having higher barometric pressure than around the holding surface 32s). With this configuration, while passing the delivery position Pout, the holding pad 32 ejects air outwardly in the turning-radius direction Dr toward the single-cut sheet 7, through all the suction holes 33h on the holding surface 32s substantially at the same time. With this ejected air, the separation of the single-cut sheet 7 from the holding surface 32s can be performed more smoothly. Also, since such ejected air acts to push the single-cut sheet 7 toward the second continuous sheet 8a, the substantial jumping of the single-cut sheet 7 will become smoother.

It is also desirable that, as shown in FIG. 2, a pair of press rollers 60 and 60 are placed at a position downstream from the neighboring position Pn near the delivery position Pout on the running path of the second continuous sheet 8a. The press rollers 60 and 60 are driven and rotates about its rotary axis C60 extending in the CD direction, along the running direction of the second continuous sheet 8a. The press rollers 60 and 60 are disposed so that the outer circumferential surfaces thereof face each other. With such a configuration, when passing the nip between the press rollers 60 and 60, the second continuous sheet 8a and the single-cut sheet 7 placed thereon are pressed by the outer circumferential surfaces of the press rollers 60 and 60 in a direction which the single-cut sheet 7 is placed on the second continuous sheet 8a. Thus, the single-cut sheet 7 can be attached to the continuous sheet 8a firmly.

The suction amount of the suction holes 54 of the suction belt conveyer 50 may be increased/decreased according to an increase/decrease of the running speed V8a of the second continuous sheet 8a. This makes it possible to prevent variations in the attachment pitch P7 of the single-cut sheets 7 that may occur when the running speed V8a of the second continuous sheet 8a is increased/decreased. This will be described in detail as follows.

For example, when the suction amount is constant, a jumping time of the single-cut sheet 7 is constant at any time, the jumping time being a time from its separation from the holding pad 32 until its arrival at the second continuous sheet. On the other hand, when the running speed V8a of the second continuous sheet 8a is high, the second continuous sheet 8a moves farther in the running direction than when the speed V8a is low. Therefore, at the time of increasing the running speed V8a of the second continuous sheet 8a, the attachment pitch P7 becomes small, and conversely, at the time of decreasing the running speed V8a, the attachment pitch P7 becomes large. In other words, there is the possibility that the attachment pitch P7 varies.

To address the above problem, increase or decrease the suction amount per unit time of the suction holes 54 in accordance with (e.g., in linkage with) an increase/decrease of the running speed V8a. This makes it possible to shorten the jumping time of the single-cut sheet 7 when the running speed V8a is high, and to prolong the jumping time when the speed V8a is low. Therefore, it is possible to prevent the displacement of the attached position of the single-cut sheet 7 from the target position, which results in reduction of the variations in the attachment pitch P7.

The control of the increase/decrease of the suction amount as described above can be implemented by a control section such as a computer and a programmable logic controller (PLC). For example, when the suction through the suction holes 54 is performed by a fan of a blower, a processor of the control section increases/decreases the number of revolutions (rpm) of the fan according to (e.g., in proportion to) the running speed V8a based on a program read from a memory, and thereby the control section controls the increase/decrease of the suction amount.

—Second Embodiment—

Figure 4:
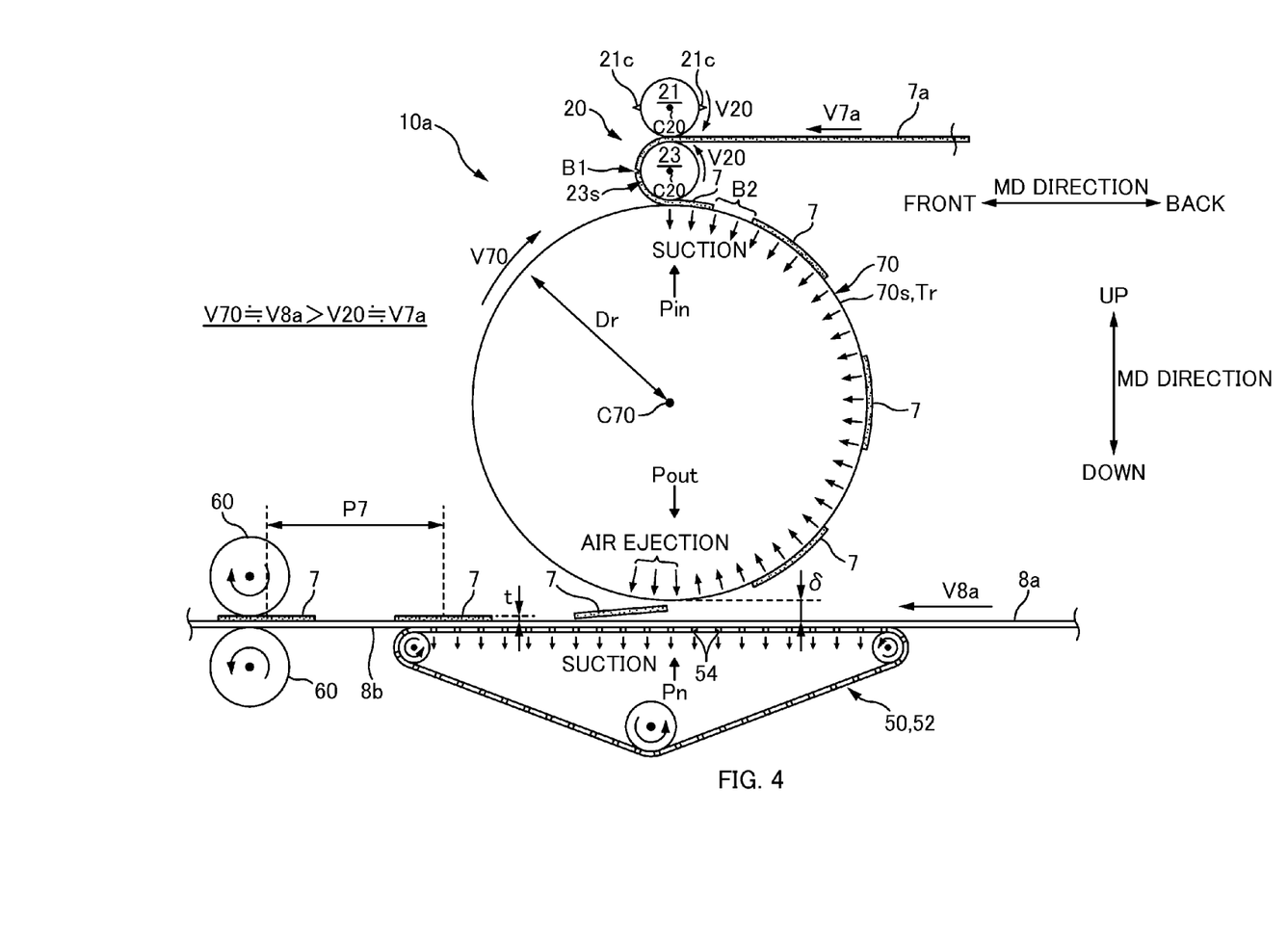
FIG. 4 is a schematic side view of a manufacturing apparatus 10a for a composite body 8b of a continuous sheet 8a in the second embodiment.

FIG. 4 is a schematic side view of a manufacturing apparatus 10a for a composite body 8b of a continuous sheet 8a of the second embodiment.

While the configuration in which the holding pads 32 as the holding section moves round along the path Tr is illustrated in the first embodiment, the second embodiment is mainly different from the first embodiment in the following points: the holding section is an outer circumferential surface 70s of a roller 70 (hereinafter also referred to as a transfer roller 70); and the path Tr of the holding section is formed along the outer circumferential surface 70s in the circumferential direction.

That is, the smooth outer circumferential surface 70s of the transfer roller 70 is configured to have a plurality of suction holes (not shown) over the entire circumference, so that the single-cut sheets 7 can be sucked to and held on the surface in the surface contact state by suction through the suction holes. While being driven and rotating, the transfer roller 70 receives and holds the single-cut sheet 7 fed from the cutter apparatus 20 onto the outer circumferential surface 70s at a predetermined position thereof in the circumferential direction as the receipt position Pin. The, the transfer roller 70 transports the held single-cut sheet 7 to the delivery position Pout in the circumferential direction by the rotation. Thereafter, the transfer roller 70 delivers the single-cut sheet 7 by attaching the single-cut sheet 7 to the second continuous sheet 8a that is running through the neighboring position Pn near the delivery position Pout.

In the same way as the first embodiment, the second embodiment is configured so that, in the above delivery, the single-cut sheet 7 is attached to the second continuous sheet 8a without being pinched between the second continuous sheet 8a and the outer circumferential surface 70s, which serves as the holding section. This prevents the occurrence of wrinkles at the time of delivery.

The manufacturing apparatus 10a of the second embodiment having the above configuration will be described hereinafter.

As shown in FIG. 4, the cutter apparatus 20 has approximately the same structure as that of the first embodiment. Moreover, as the running mechanism by which the second continuous sheet 8a runs, the suction belt conveyer 50 is used, which is also the same as in the first embodiment. Thus, these apparatuses will be described where necessary.

The transfer roller 70 is disposed between the cutter apparatus 20 and the suction belt conveyer 50, and is driven and rotates about its rotary axis C70 extending in the CD direction at a predetermined peripheral speed V70. The peripheral speed V70 is set so as to be higher than the peripheral speed V20 of the anvil roller 23 of the cutter apparatus 20 and approximately the same as the running speed V8a of the second continuous sheet 8a. Also, the peripheral speed V20 of the anvil roller 23 is set so as to be approximately the same as the feeding speed V7a of the first continuous sheet 7a that is the base material of the single-cut sheets 7.

Accordingly, the single-cut sheet 7 produced by cutting off a leading portion from the first continuous sheet 7a by the cutter blade 21c of the cutter roller 21 is transported by the rotation of the anvil roller 23 while the single-cut sheet 7 is being sucked to and held on the outer circumferential surface 23s of the anvil roller 23 in an integrated manner. When the single-cut sheet 7 arrives at the receipt position Pin of the transfer roller 70 that is the position facing the transfer roller 70, the suction of the portion of the outer circumferential surface 23s that passes the receipt position Pin is sequentially stopped. Therefore, the portion of the single-cut sheet 7 that has passed the receipt position Pin moves to the outer circumferential surface 70s of the transfer roller 70 sequentially, and is sucked to and held on the outer circumferential surface 70s.

At this time, however, since most of the single-cut sheet 7 is still held on the outer circumferential surface 23s of the anvil roller 23, the suction force of the outer circumferential surface 23s of the anvil roller 23 is larger than that of the transfer roller 70 as a whole. Therefore, for a while, the single-cut sheet 7 moves along the outer circumferential surface 70s of the transfer roller 70 at the peripheral speed V20 of the anvil roller 23, relatively sliding in a direction the single-cut sheet 7 delays with respect to the outer circumferential surface 70s of the transfer roller 70. On the other hand, at this time, the preceding another single-cut sheet 7 is sucked to and held on the outer circumferential surface 70s of the transfer roller 70 through it's entire length as shown in FIG. 4; the preceding single-cut sheet 7 is moving at the peripheral speed V70 of the transfer roller 70. Therefore, the spacing B2 between these single-cut sheets 7 gradually widens, and finally, after the spacing B2 has widened up to the spacing corresponding to the attachment pitch P7, the single-cut sheet 7 is attached to the second continuous sheet 8a in a discontinuous arrangement.

As mentioned earlier, the single-cut sheet 7 moves from the transfer roller 70 to the second continuous sheet 8a without being pinched therebetween at the delivery position Pout. To implement this operation, a similar device to that in the first embodiment is provided also for the delivery position Pout in the second embodiment.

That is, as shown in FIG. 4, the spacing 5 at the delivery position Pout between the outer circumferential surface 70s of the transfer roller 70 and the second continuous sheet 8a is set so as to be more than 1.0 times and less than 3.0 times as large as the maximum thickness t of the single-cut sheet 7 (more preferably, more than 1.0 times and less than 2.0 times as large as the maximum thickness t of the single-cut sheet 7); and the suction of the suction belt conveyer 50 acts, through the second continuous sheet 8a, on the single-cut sheet 7 passing the delivery position Pout. Therefore, by the suction force by this suction, the single-cut sheet 7 moves from the outer circumferential surface 70s of the transfer roller 70 to the second continuous sheet 8a. As a result, the single-cut sheet 7 and the second continuous sheet 8a are bonded together without pinching, which results in prevention of wrinkling.

As in the case of the first embodiment, it is desirable that the suction force by the suction of the outer circumferential surface 70s of the transfer roller 70 is weakened at the delivery position Pout. The detail is as follows: when the suction holes are passing in a range from the receipt position Pin to immediately before the delivery position Pout in the circumferential direction, suction is performed to impart the suction force to the outer circumferential surface 70s; when the suction holes are passing or have passed the delivery position Pout, the suction holes sequentially stop the suction to make the suction force zero. Therefore, the single-cut sheet 7 is smoothly separated and moves from the outer circumferential surface 70s at the delivery position Pout to the second continuous sheet 8a. It goes without saying that the suction holes restart the suction when they pass through the receipt position Pin.

It is more desirable that, when the suction holes are passing the delivery position Pout, the suction holes not only stop the suction but also eject air outwardly in the turning-radius direction Dr toward the single-cut sheet 7, as shown in FIG. 4. With this ejected air, the separation of the single-cut sheet 7 from the outer circumferential surface 70s of the transfer roller 70 will be performed more smoothly. Also, since such ejected air acts to push the single-cut sheet 7 toward the second continuous sheet 8a, the movement of the single-cut sheet 7 will become smoother.

—Example Applications to Manufacturing Method for Absorbent Article 1—

The composite body 8b of the continuous sheet 8a manufactured by the manufacturing apparatuses 10 and 10a of the first and second embodiments is used as a component of an absorbent article 1. The process of manufacturing the absorbent article 1 using the composite body 8b of the continuous sheet 8a will be described hereinafter taking a disposable diaper 1 as an example of the absorbent article 1.

Figure 5A:
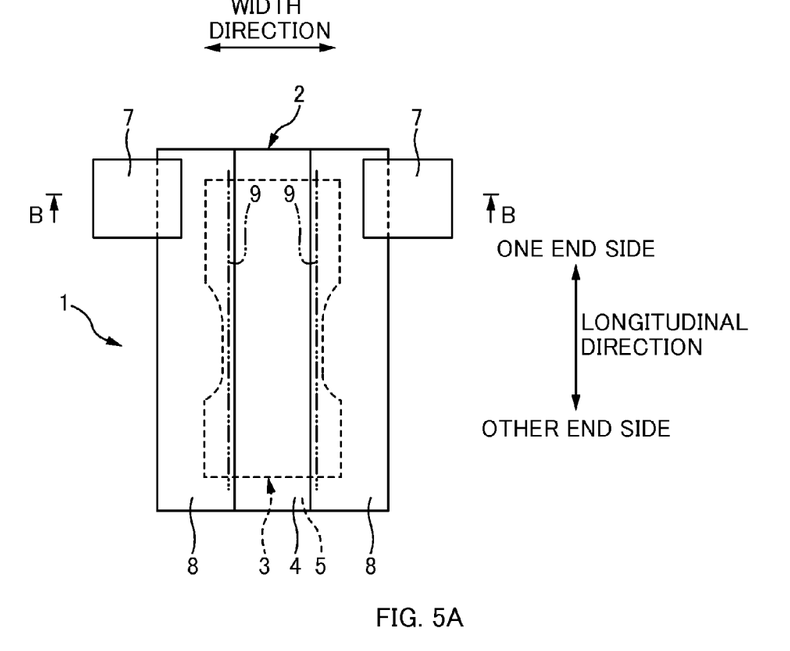
FIG. 5A is a plan view of a disposable diaper 1 in its opened condition, as an example of the absorbent article.
Figure 5B:
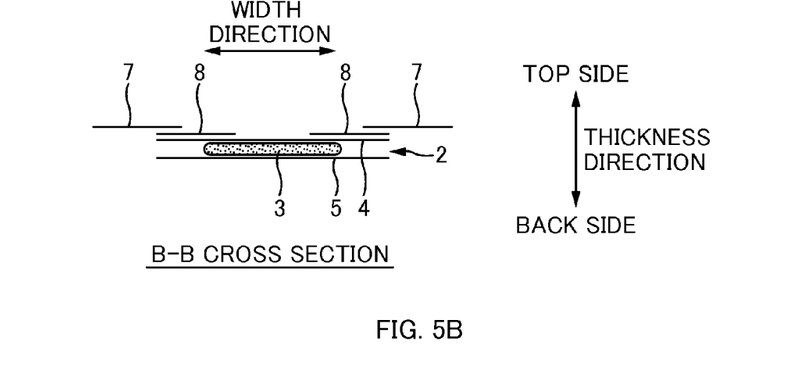
FIG. 5B is a cross-sectional view taken along line B-B in FIG. 5A.

FIG. 5A is a plan view of the disposable diaper 1 in its developed state, and FIG. 5B is a cross-sectional view taken along line B-B in FIG. 5A.

The disposable diaper 1 has an absorbent main body 2 to be positioned between the wearer's legs. The absorbent main body 2 includes: an absorbent body 3 made of liquid-absorbing fibers such as pulp fibers; a liquid-permeable top sheet 4 covering the top surface of the absorbent body 3 on the wearer's skin side; and a liquid-impermeable back sheet 5 covering the bottom surface of the absorbent body 3. The planar shape of the absorbent main body 2 has a longitudinal direction and a width direction. Side sheets 8 made of a nonwoven fabric are attached to end portions of the top sheet 4 of the absorbent main body 2 in the width direction, and further side flaps 7 made of a nonwoven fabric are attached to the side sheets 8 so as to protrude outward from the end edges of the absorbent main body 2 in the width direction.

The side flaps 7 are provided on at least one end portion of the absorbent main body 2 in the longitudinal direction. The side flaps 7 are to be fastened to the other end portion of the absorbent main body 2 in the longitudinal direction via a fastening member (not shown) such as a hook-and-loop fastener, to form a waist opening and a pair of leg openings, whereby the disposable diaper 1 becomes ready to be worn.

Note that, depending on the circumstances, as shown in FIG. 5A, elongated elastic members, which is rubber threads 9, etc., may be secured along the inner edges of the side sheets 8 in the width direction. In this case, while the disposable diaper 1 is being worn, the edges of the side sheets 8 stand from the absorbent main body 2 and serves as three-dimensional gathers.

Among the components of the disposable diaper 1, each side sheet 8 having the side flap 7 attached thereto is manufactured by the manufacturing apparatus 10 (10a) described above. That is, this portion corresponds to the composite body 8*b* of the continuous sheet 8*a* in FIG. 2 (FIG. 4). More specifically, the second continuous sheet 8*a* corresponds to base material 8*a* of the side sheet 8 (hereinafter referred to as a side sheet base material 8*a*) which has not been divided on a product-by-product basis, and the single-cut sheets 7 correspond to the side flaps 7.

Therefore, as shown in FIG. 2 (FIG. 4), to the manufacturing apparatus 10 (10*a*) described above, a base material 7*a* of the side flaps 7 is fed as the first continuous sheet 7*a* continuously in the MD direction, and the side sheet base material 8*a* is fed as the second continuous sheet 8*a* continuously in the MD direction. The manufacturing apparatus 10 (10*a*) then attaches the side flaps 7 to the side sheet base material 8*a* at the attachment pitch P7 in the MD direction, and manufactures the composite body 8*b* of the side sheet base material 8*a*.

Figure 6:
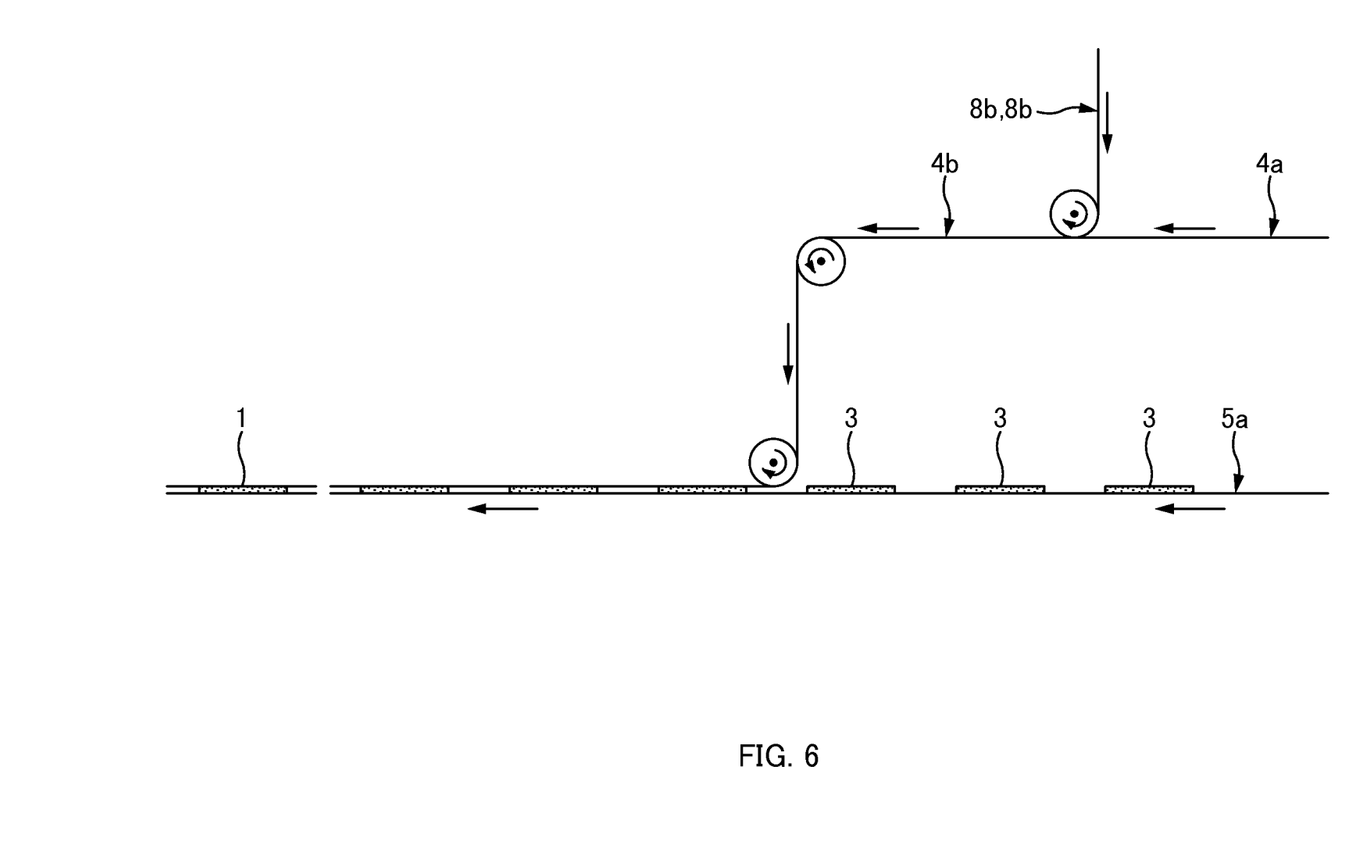
FIG. 6 is a schematic view of a production line for the disposable diaper 1.

A pair of composite bodies 8*b* of the side sheet base materials 8*a* are manufactured in a state where they are arranged side by side in the CD direction in the production line for the diapers 1. Then, as shown in the schematic side view of the production line in FIG. 6, while being transported in the MD direction, the pair of composite bodies 8*b* are attached to end portions of a continuous sheet 4*a* in the width direction, the continuous sheet 4*a* being the base material of the top sheet 4. A resultant continuous sheet 4*b* of the top sheet 4 with the composite bodies 8*b* attached thereon is transported in the MD direction, and, during the transportation, is attached together to a continuous sheet 5*a* of the back sheet 5 on which the absorbent bodies 3 are placed at a product pitch. The resultant sheet is then cut at the product pitch, to manufacture the disposable diapers 1.

—Other Embodiments—

While the embodiments of the present invention have been described, it is understood that the present invention is not limited to those but can be modified as follows.

The holding force (suction force) of the holding pad 32 is made zero at the delivery position Pout in the above embodiments as an example of weakening the holding force. However, it is not necessary for the holding force to be zero. That is, if only the magnitude of the holding force imparted to the holding surface 32*s* at the delivery position Pout has decreased from that in the range from the receipt position Pin to a position immediately before the delivery position Pout, the separation property of the single-cut sheet 7 from the holding surface 32*s* will improve by the amount corresponding to this decrease. It is therefore unnecessary to make the holding force zero.

Although the continuous sheet 7*a* made of a nonwoven fabric was used as the base material 7*a* of the single-cut sheets 7 in the above embodiments, the material is not limited to the nonwoven fabric, but a woven fabric or a film, for example, may be used. However, from the standpoint of the suction property at the delivery position Pout, it is desirable to use a material having a low air-permeability because the suction force acting on the single-cut sheet 7 made of such a material will enhance.

Although the disposable diaper 1 was taken as an example of the absorbent article in the above embodiment, the absorbent article is not limited to this as long as it absorbs excreted fluid and body fluid. For example, the manufacturing apparatuses 10 and 10*a* of the above embodiments may be applied to a production line for sanitary napkins.

LIST OF REFERENCE NUMERALS

1 disposable diaper (absorbent article),
2 absorbent main body, 3 absorbent body,
4 top sheet, 4*a* continuous sheet of top sheet,
5 back sheet, 5*a* continuous sheet of back sheet,
7 single-cut sheet (side flap),
7*a* first continuous sheet (base material of side flap),
8 side sheet, 8*a* second continuous sheet (continuous sheet, base material of side sheet),
8*b* composite body of continuous sheet, 9 elastic member,
10 manufacturing apparatus, 10 manufacturing apparatus,
20 cutter apparatus, 21 cutter roller, 21*c* cutter blade
23 anvil roller, 23*s* outer circumferential surface,
30 attaching apparatus, 31 rotary drum,
32 holding pad (holding section), 32*s* holding surface,
33 holding-force imparting mechanism (holding-force adjustment mechanism),
33*h* suction hole, 33*p* air flow path, 33*rn* negative pressure chamber, 33*rp* Positive pressure chamber,
50 suction belt conveyer (sucking mechanism, suction mechanism, running mechanism),
52 endless belt, 54 suction hole,
60 press roller
70 transfer roller, 70*s* outer circumferential surface (holding section)
Pin receipt position, Pout delivery position, Pn neighboring position,
P30 position,
C20 rotary axis, C30 turning axis, C60 rotary axis, C70 rotary axis,
Tr circling track, Tr50 path

The invention claimed is:

1. A manufacturing method for a composite body of a continuous sheet associated with an absorbent article, the composite body being manufactured by attaching a single-cut sheet to the continuous sheet at a predetermined attachment pitch, the method comprising:
   providing a cutter roller and an anvil roller to form the single-cut sheet therewith;
   receiving the single-cut sheet at a receipt position by a holding section in surface-to-surface contact from the anvil roller, the holding section moving along a path, the holding section having an arc-shaped surface extending along the path;
   weakening a holding force by which the single-cut sheet is held;
   exerting a suction force on the single-cut sheet through the continuous sheet, the suction force causing the single-cut sheet to be sucked toward the continuous sheet; and
   when the holding section passes a delivery position set on the path,
   separating the single-cut sheet from the holding section, and
   delivering the single-cut sheet to the continuous sheet by attaching the single-cut sheet to the continuous sheet without pinching the single-cut sheet between the holding section and the continuous sheet due to the weakening and the exerting, the continuous sheet being running through a neighboring position near the delivery position,
   wherein
   a gap between the holding section and an adjacent holding section at the delivery position is wider than the gap between the holding section and the adjacent holding section at the receipt position,
   a running speed of the continuous sheet being set so as to be higher than a peripheral speed of the anvil roller,
   the holding section has a holding surface, a plurality of suction holes formed on the holding surface, and an air flow path that is formed inside the holding section and communicates with the suction holes, when the holding section arrives at the delivery position, the air flow path communicates with a positive pressure chamber and the holding section ejects air outwardly toward the single-cut sheet, through all the suction holes on the holding surface substantially at the same time such that the elected air pushes the single-cut sheet toward the continuous sheet and the single-cut sheet jumps from the holding section to the continuous sheet, suction holes are provided to a suction belt conveyer and at the neighboring position, the suction holes sucking air through the continuous sheet in a direction in which the single-cut sheet is separated from the holding section passing the delivery position, and a suction amount of the suction applied to the holes provided to the suction belt conveyer is increased or decreased according to an increase or decrease of a running speed of the continuous sheet such that the higher the running speed becomes, the shorter a jumping time of the single-cut sheet toward the continuous sheet becomes.

2. A manufacturing method for a composite body of a continuous sheet associated with an absorbent article according to claim 1, wherein a pair of press rollers that rotate with their outer circumferential surfaces facing each other are disposed at a position downstream from the neighboring position on a running path of the continuous sheet, and when passing a nip between the press rollers, the continuous sheet and the single-cut sheet that is placed on the continuous sheet are pressed by the outer circumferential surfaces of the press rollers in a direction which the single-cut sheet is placed on the continuous sheet.

3. A manufacturing method for a composite body of a continuous sheet associated with an absorbent article according to claim 1, wherein a size of a spacing between the holding section and the continuous sheet at the delivery position is set to a value more than 1.0 times and less than 3.0 times as large as the maximum thickness of the single-cut sheet.

4. A manufacturing method for a composite body of a continuous sheet associated with an absorbent article according to claim 1, wherein a suction mechanism is provided at the neighboring position, the suction mechanism sucking air through the continuous sheet in a direction in which the single-cut sheet is separated from the holding section passing the delivery position, and an air permeability of the continuous sheet is higher than that of the single-cut sheet.

5. A manufacturing method for a composite body of a continuous sheet associated with an absorbent article according to claim 1, wherein a suction mechanism is provided at the neighboring position, the suction mechanism sucking air through the continuous sheet in a direction in which the single-cut sheet is separated from the holding section passing the delivery position, and a suction amount of the suction mechanism is increased/decreased according to an increase/decrease of a running speed of the continuous sheet.

6. A manufacturing method for an absorbent article using a composite body that is manufactured in a method according to claim 1, wherein the absorbent article includes
an absorbent main body that has an absorbent body for absorbing a liquid and is brought into contact with a crotch of a wearer,
a pair of side sheets attached to both end portions of the absorbent main body in the width direction, and
a side flap attached to each of the side sheets so as to protrude outwardly in the width direction from an edge of the absorbent main body In the width direction, the continuous sheet is a base material of the side sheet that has not been divided into a piece of the side sheet, the single-cut sheet is the side flap, the absorbent main body has a top sheet covering the absorbent body, and the composite body is attached to a continuous sheet of the top sheet after manufacturing the composite body.

* * * * *